(12) United States Patent
Dor et al.

(10) Patent No.: US 6,334,871 B1
(45) Date of Patent: *Jan. 1, 2002

(54) RADIOPAQUE STENT MARKERS

(75) Inventors: Ofer Dor, Ramat-Gan; Amir Loshakove, Bney Brak; Oren Globerman, Holon; Mordechay Beyar; Rafael Beyar, both of Haifa, all of (IL)

(73) Assignee: Medtronic, Inc., Minneapolis, MN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/697,989

(22) Filed: Sep. 3, 1996

Related U.S. Application Data

(63) Continuation-in-part of application No. 08/632,739, filed on Apr. 15, 1996.

(30) Foreign Application Priority Data

Mar. 13, 1996 (IL) ................................. 117472

(51) Int. Cl.$^7$ ................................. A61F 2/06
(52) U.S. Cl. ................................. 623/1.34
(58) Field of Search ................................. 623/11, 1, 12, 623/1.34, 1.1, 1.15

(56) References Cited

U.S. PATENT DOCUMENTS

| 264,502 A | 9/1882 | Woolson |
|---|---|---|
| 3,902,501 A | 9/1975 | Citron et al. |
| 4,051,592 A | 10/1977 | Briles |
| 4,531,243 A * | 7/1985 | Weber .......................... 623/22 |
| 4,733,665 A | 3/1988 | Palmaz |
| 4,828,566 A * | 5/1989 | Griss ............................ 623/23 |
| 5,080,674 A * | 1/1992 | Jacobs .......................... 623/20 |
| 5,104,404 A | 4/1992 | Wolff |
| 5,306,250 A * | 4/1994 | March .......................... 604/104 |
| 5,366,473 A * | 11/1994 | Winston ........................ 623/12 |
| 5,443,520 A * | 8/1995 | Zweymüller .................. 623/22 |
| 5,556,413 A | 9/1996 | Lam |
| 5,607,442 A | 3/1997 | Fischell et al. |
| 5,632,771 A | 5/1997 | Boatman et al. |
| 5,725,570 A | 3/1998 | Heath |
| 5,725,572 A | 3/1998 | Lam et al. |
| 5,800,508 A | 9/1998 | Goicoechea et al. |
| 5,824,042 A | 10/1998 | Lombardi et al. |
| 5,824,077 A | 10/1998 | Mayer |
| 6,066,168 A | 5/2000 | Lau et al. |
| 6,203,569 B1 | 3/2001 | Wijay |

FOREIGN PATENT DOCUMENTS

| EP | 0 679 372 | 11/1995 |
|---|---|---|
| GB | 1205743 | 9/1970 |
| WO | WO 95/03010 | 2/1995 |

* cited by examiner

Primary Examiner—Michael J. Milano
(74) Attorney, Agent, or Firm—Mueting, Raasch & Gebhardt, P.A.

(57) ABSTRACT

Stents which are inserted into a body lumen preferably are made of materials which are not radiopaque enough, such as stainless steel 316L. X-ray visualization of a stent enables an accurate positioning of the stent and also a follow-up of its functioning within the patient's body. The radiopaque markers described here are rivets made of a material which is more radiopaque than the stent substance so the location of the stent can be identified. Preferably the stents are heat treated so that atoms from the stent material migrate into the marker material and vice versa.

17 Claims, 4 Drawing Sheets

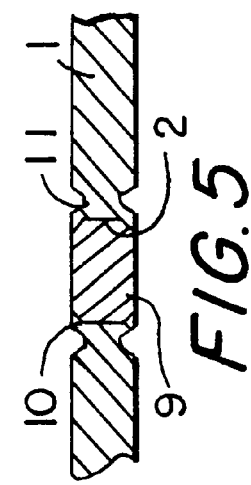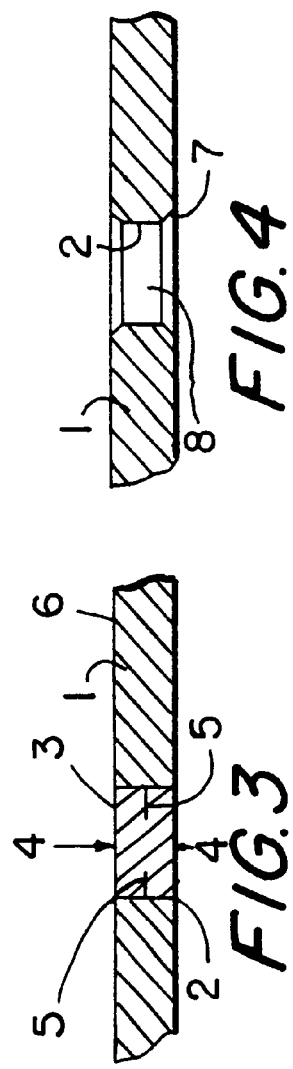

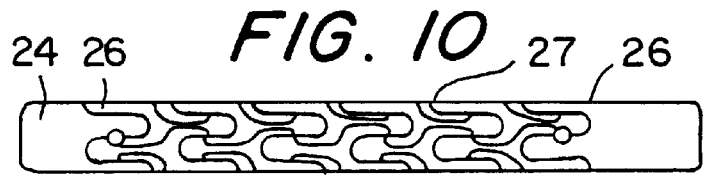
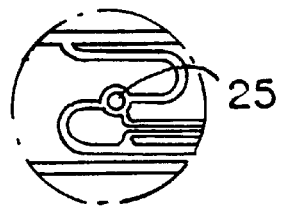
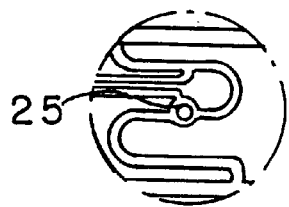
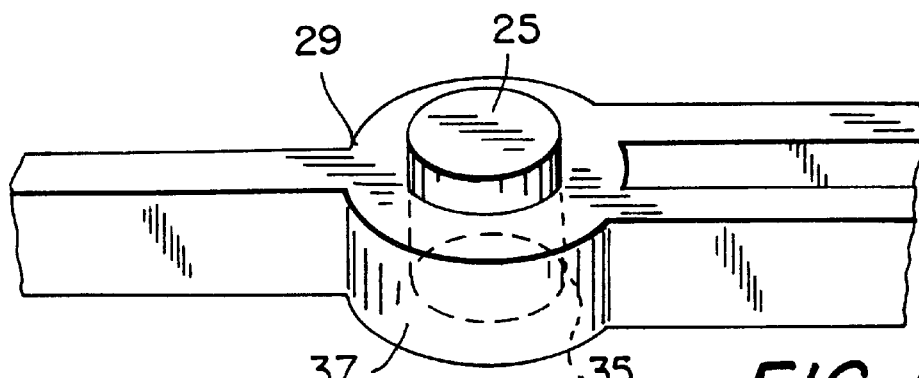
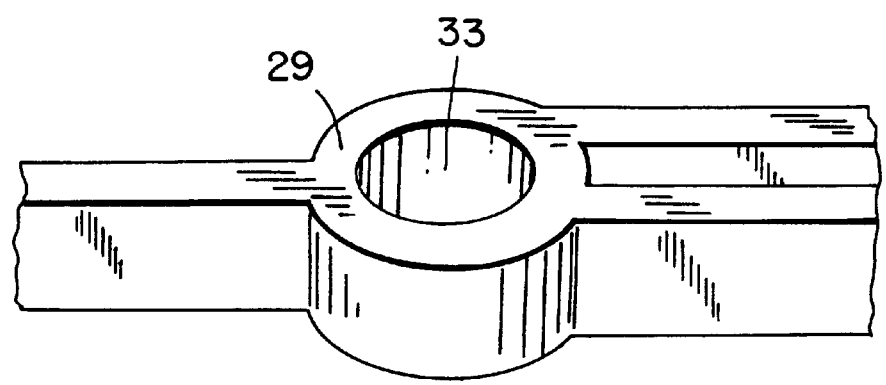

RADIOPAQUE STENT MARKERS

CROSS-REFERENCE TO RELATED APPLICATION

This application is a continuation-in-part of U.S. patent application Ser. No. 08/632,739, filed Apr. 15, 1996.

FIELD OF THE INVENTION

This invention relates to endoprosthesis devices, generally called stents, and, more particularly, to radiopaque markers for use with endoprosthesis devices.

BACKGROUND OF THE INVENTION

Stents are generally tubular shaped devices that function to hold open a segment of a blood vessel or other anatomical lumen and are useful in the treatment of atherosclerotic stenoses in blood vessels. Stents are particularly suitable for use in supporting and holding back a dissected arterial lining that can occlude the fluid passageway therethrough.

To accomplish precise placement of stents, various means are employed for identifying the position of the stent within a blood vessel. One means used for accomplishing precise placement of a stent is the attachment to the stent of radiopaque markers so that, through the use of fluoroscopy, the position of the stent within a blood vessel can be identified. Once the stent with its radiopaque markers has been implanted, identification of the stent position during subsequent checkups of the treated segment is easily accomplished because the markers remain visible under fluoroscopy.

In European patent application No. 95302708, assigned to ACS, Inc., a method of coating the stent edges as markers is described. However, this method has several practical disadvantages. First, heavy coating of radiopaque markers onto a stent is somewhat difficult to accomplish. In addition, the radiopaque material might not be attached properly to the stent material and may detach, leaving no way of identifying the position of the stent within the blood vessel. Furthermore, the radiopaque coating may increase the rigidity of the stent, thereby making it difficult to open the stent and decreasing the stent's effectiveness.

In another method for enabling the precise identification of a stent location using radiopaque markers, commonly assigned U.S. patent application Ser. No. 08/394,799, filed Feb. 27, 1995, discloses a hollow stent having radiopaque material inserted within the hollow stent wire. Because this method of providing radiopaque marking requires that the stent wire is hollow, this method might not be useful where a hollow stent is not desirable.

Another well-known method for enabling the precise identification of a stent location within a blood vessel is producing the stent itself from a radiopaque material such as tantalum. However, a disadvantage of this method is that tantalum is a relatively soft material and it is, therefore, necessary to use more of this metal to achieve sufficient support from the stent.

OBJECTS OF THE INVENTION

It is an object of the invention to provide improved stents.

It is also an object of the invention to provide stents having radiopaque markers.

It is a further object of the invention to provide stents where the distal ends of the stents comprise rivets of material that is more radiopaque than the material from which the stents are made.

These and other objects of the invention will become more apparent in the discussion below.

SUMMARY OF THE INVENTION

The radiopaque markers described below are designed for stents produced from a material that is not sufficiently radiopaque to be seen through the use of fluoroscopy, e.g., a material such as Stainless Steel 316L, nitinol, or a cobalt-chromium alloy. In order to identify the position of the stent during its insertion into the body and after it has been implanted, however, it is enough to mark the stent edges so that they may be seen under X-ray. The location of the stent will thus be evident based upon the pinpoint locations of its two ends.

According to this invention the edges of the stents are marked by inserting rivets through the ends or edges of the stents, which rivets are made of a material that is more radiopaque than the stent material. For example, if the stent material is S.S. 316L, the rivets can be made of gold, gold alloy, tantalum, tantalum alloy, platinum, or platinum alloy.

BRIEF DESCRIPTION OF THE DRAWINGS

The above and other objects and advantages of the invention will be apparent upon consideration of the following detailed description, taken in conjunction with the accompanying drawings, in which the reference characters refer to like parts throughout and in which:

FIG. 3 shows a cross-sectional view of a first embodiment of a rivet inserted through the opening of FIG. 1;

FIG. 4 shows a cross-sectional view of a second embodiment of a rivet inserted through the opening of FIG. 1;

FIG. 5 shows a cross-sectional view of a third embodiment of a rivet inserted through the opening of FIG. 1;

FIG. 6 shows a cross-sectional view of a fourth embodiment of a rivet inserted through the opening of FIG. 1;

FIG. 7 shows a cross-sectional view of a fifth embodiment of a rivet inserted through the opening of FIG. 1;

FIG. 10 is a perspective view of an embodiment of the invention on a mandril;

FIG. 10A is an enlarged detailed view of one end of the stent depicted in FIG. 10.

FIG. 10B is an enlarged detailed view of another end of the stent depicted in FIG. 10.

FIG. 11 is a perspective exploded view of a marker according to the invention, prior to heat treatment; and FIG. 12 is a perspective exploded view of a marker according to the invention, after heat treatment.

DETAILED DESCRIPTION OF THE INVENTION

Figure 2:
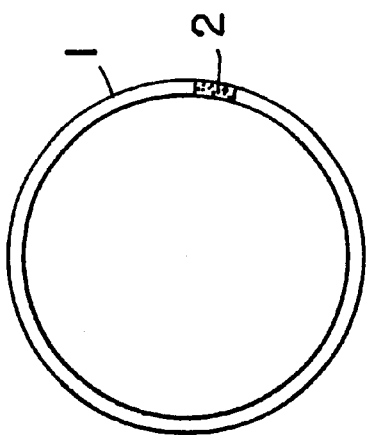
FIG. 2 shows a cross-sectional view taken along line 2—2 of FIG. 1 across the entire stent.
Figure 1:
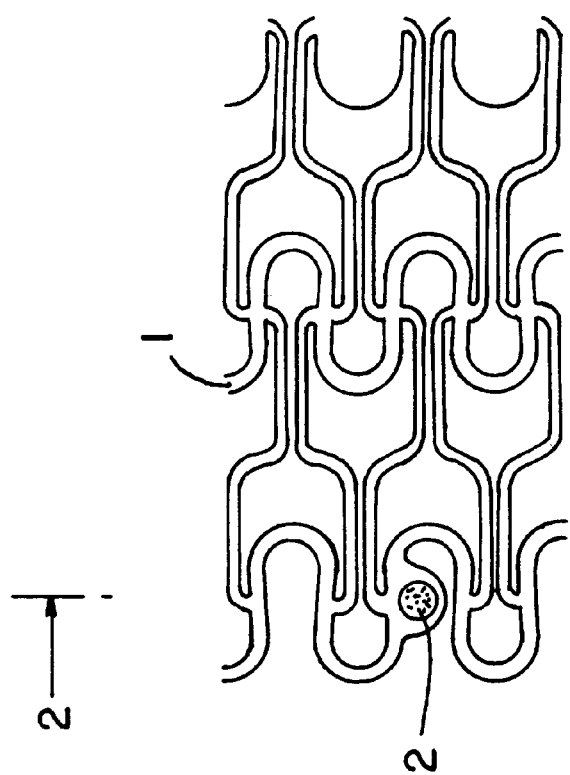
FIG. 1 shows a side elevational view of a portion of a balloon-expandable stent structure having a round opening at each distal end or edge in accordance with an embodiment of this invention.

Balloon-expandable stent structures are well known in the art. In this invention, as illustrated in FIG. 1, a balloon-expandable stent structure 1 has an opening 2 at each stent end or edge. In a first embodiment of the invention, the openings 2 are round. FIG. 2 shows a cross-section of the stent 1 and shows opening 2 passing radially from the external stent surface into the internal stent surface.

According to the invention a marker having radiopaque qualities is inserted through the opening at each end or edge of the stent to mark the ends of the stent so that the position of the stent can be determined by the location of its ends when the markers are seen under X-ray. Because the markers are placed securely into and through holes or openings, they are referred to as "rivets".

FIG. 3 illustrates the placement of a rivet 3 into a stent opening 2. Rivet 3 comprises a short rod made from a radiopaque material, which is compressed into the opening 2 in the axial direction 4, thereby compressing the radiopaque material and causing a circumferential force 5 that enables rivet 3 to be held within opening 2 of stent 6. Because retention of the marker rivet requires an opening whose aperture size does not vary while the rivet is inserted therein, the preferred location of the marker rivet is a region of the stent that is not deformed during expansion of the stent. In particular, for a balloon-expandable stent, this will usually be at an edge of the stent, at the end of the stent's lattice-like structure.

As shown in FIG. 4, an alternative manner of assuring that the rivet remains in the stent opening 2 is to form the rivet edges 7 with a cone-like, outwardly radiating shape, i.e., with beveled edges. Then, after the radiopaque rivet 8 is compressed into opening 2, the rivet 3 cannot leave the stent due to the friction between the edges 7 of the rivet and the outer edges of the inner walls of opening 2.

Another means of securing the rivet within the lumen is shown in FIG. 5, in which the marker rivet 9 is made with chamfered edges 10. After rivet 9 is inserted into the opening 2, the stent 1 is pressed at points 11 so the marker rivet 9 cannot displace from the stent.

In a further embodiment of the invention illustrated in FIG. 6, an enlarged head portion 13 of rivet 12 protrudes from opening 2 on one side of the stent in a diameter larger than that of the rivet portion situated within opening 2. Thus, when the stent is viewed through X-ray, a larger height and greater diameter of the rivets and, therefore, a better visualization of the markers of the ends of the stent, is achieved. FIG. 7 illustrates a variation of this embodiment of the rivet in which the enlarged head portion 13 protrudes from both sides of the stent, achieving even larger height and greater diameter of the rivet and still better visualization of the rivet, and thus the stent ends, under X-ray.

Figure 8:
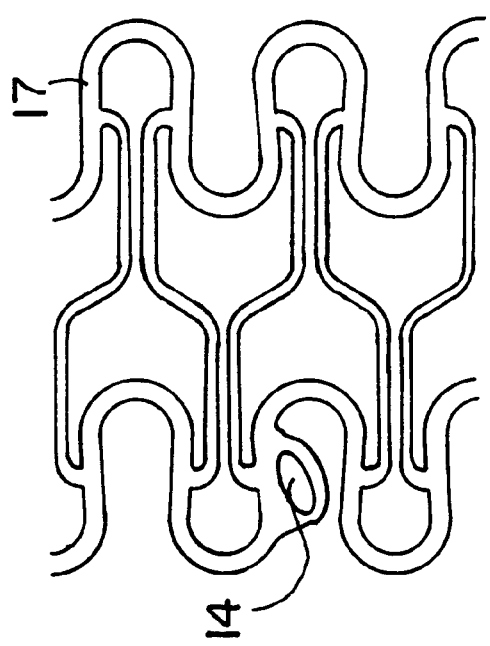
FIG. 8 shows a side elevational view of a portion of a balloon-expandable stent structure having a second embodiment of an opening at each edge.

FIG. 8 illustrates a second embodiment of the invention, in which an opening 14 of stent 17 is non-round, such as oval. The non-round opening 14 allows a non-round rivet to be inserted therein. This serves to enlarge the rivet surface without interfering with the fluid flow within the stent.

Figure 9:
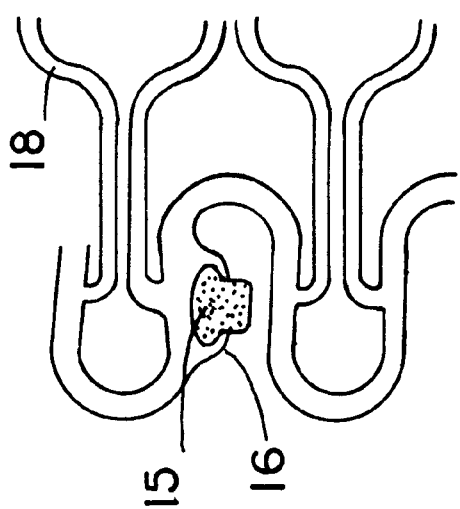
FIG. 9 shows a side elevational view of a portion of a balloon expandable stent structure having a third embodiment of an opening and showing a marker inserted through the opening.

In the embodiments of this invention illustrated in FIGS. 1 through FIG. 8, marker rivets are completely surrounded by the stent material so that they either are contained within the stent material or project only from the external and internal surfaces of the stent. Another embodiment of the invention and an additional type of marker rivet is shown in FIG. 9, in which the place of insertion of the marker is not a loop or an opening passing radially through the stent material 18 but is rather a circumferential space encompassed by two circumferential detent projections 16. The corresponding marker 15 is pressed circumferentially into the space and is held there by specially designed projections 16 into adequate shape in the marker. This method enables an insertion of a marker with larger visible surface area by allowing the larger surface area to fit along and be co-extensive with the stent circumference as opposed to projecting radially into and out of the stent shape.

As described above, the rivets are preferably compressed into the stent material. Optionally, in addition to or in place of compression, the surface between the rivets and the stent can be heated to weld or fuse the rivets into position. Preferably such heating would be focused heating, for example, with a laser, where only the rivet and stent material would be present.

In the embodiment of the invention set forth in FIGS. 10 to 12, a marker 25 is preferably positioned at each end 26 of an expandable stent 27, which is shown on a mandril 24. The markers 25 are positioned within ring structures 29 in the lattice of stent 27.

It is especially preferred that stent 27 and marker 25 be comprised of materials suitable for securely positioning each marker 25 within a ring structure 29 after heat treatment. For example, if the marker 25 and ring structure 29 comprise gold and stainless steel 316L, respectively, as shown in FIG. 11, there will be migration during suitable heating. Gold from marker 25 will tend to migrate into the stainless steel 316L of ring structure 29, and components of the stainless steel 316L of ring structure 29 will migrate into marker 25, optionally forming stainless steel components on the surface of gold solid solution. The gold markers are solute and adhesive with stainless steel 316L, and the result is a thin cover layer of stainless steel components with grains of gold solution on the surface of the gold of member 25. This surface composite will behave like stainless steel in protecting the surface from, e.g., corrosion in an aggressive chemical environment and/or during an electropolishing process.

After heat treatment and electropolishing, a gold solution is formed within the ring structure 29 while a matrix 33 of gold and stainless steel components is found on the outer surface 23 of member 25, as shown in FIG. 12. Any grains of gold solution, which tend to appear in small amounts, disappear. The outer surface 23 of marker 25 will be flush with the outer surface of ring structure 29.

The marker of the embodiment of FIG. 12 is prepared by force fitting a substantially cylindrical marker 25 into a hole 35, which extends through ring structure 29. Marker 25 extends beyond either or both of outer ring structure surfaces 37. After appropriate heat treatment, for example, from about 700° to 1200° C., for from about 1 minute to 2 hours, preferably from about 1050° to 1100° C., for from about 2 to 30 minutes, under high vacuum, such as from about $10^{-4}$ to $10^{-6}$ torr in Argon atmosphere, gold within marker 25 will migrate, or diffuse, into ring structure 29, preferably from about 10 to 1000 Å. Similarly, atoms of components from the stainless steel 316L may migrate similar distances into marker 25. Also, components of the stainless steel, and/or crystals of the stainless steel 316L, may appear on one or both outer surfaces 23 of marker 25.

The process described above is particularly advantageous for at least two reasons. First, more gold can be put into each marker, which results in a better x-ray or fluoroscopic image. And second, the migration of gold into the ring structure results in a more secure fit of the marker 25 in the ring structure 29, as compared to compression or welded marker situations. To demonstrate this last point stents were prepared with markers according to the processed described above and then the force required to separate the markers from the holes in the ring structures was measured. The results were as follows:

TABLE

| Process | Separation Force |
| --- | --- |
| Compression | 250 gr |
| Compression plus welding | 400 gr |
| Heat treatment | 1–4 Kg |

Thus, the heat treatment resulted in a much more secure marker fitting.

The above-described markers are designed for both stent extremities in order to define the ends of the stent during fluoroscopy. Nonetheless these markers can be combined onto the entire stent length and also on several places located along the stent circumference, so that the stent diameter can be detected during fluoroscopy, as well. It is within the scope of the invention that a stent could have, for example, from 2 to 20 marker rivets, located from about 0.5 to 5 cm apart longitudinally and/or from 1 to 4 rivets spaced radially, preferably equidistantly, or a combination thereof.

This invention is intended primarily for use with balloon-expandable stents, although it is envisioned that the technology disclosed herein is applicable to other medical devices, including, but not limited to, self-expanding stents. An important factor is that the material of the rivet be more radiopaque than the primary material used in the device. For example, if a balloon-expandable stent is comprised of stainless steel or nitinol, then rivets comprised of gold, platinum, or titanium would be useful.

The invention herein is not limited to a particular latticework for a balloon-expandable stent. However, the invention is especially useful with the balloon-expandable stents described in co-pending U.S. patent application Ser. No. 08/543,337, filed Oct. 16, 1995, incorporated herein by reference.

It will be further apparent to one skilled in this art that the improvements provided for in the present invention, while described with relation to certain specific physical embodiments also lend themselves to being applied in other physical arrangements not specifically provided for herein, which are nonetheless within the spirit and scope of the invention taught here.

We claim:

1. A method for increasing the radiopacity of an implantable medical device produced from a material selected from the group comprising stainless steel 316L, nitinol, a cobalt-chromium alloy, and other materials of similar radiopacity, which comprises the steps of
    (a) forming openings in at least the distal edges or ends of the device,
    (b) inserting a different marker material with greater radiopacity than the rest of the device selected from the group comprising gold, gold alloys, tantalum, tantalum alloys, platinum, platinum alloys and other materials of similar radiopacity, into said openings to form a rivet in each opening, and
    (c) heating the device from step (b) for a sufficient temperature and for a sufficient time to cause atoms from the device to migrate into the marker material and atoms from the marker material to migrate into the device.

2. The method of claim 1, wherein the heating in step (c) is under vacuum.

3. The method of claim 2, wherein the heating is at from about $10^{-4}$ to $10^{-6}$ torr.

4. The method of claim 1, wherein the heating in step (c) is from about 700° C. to 1200° C. and for from about 1 minute to 2 hours.

5. An implantable medical device produced from a material selected from the group comprising stainless steel 316L, nitinol, a cobalt-chromium alloy, and other materials of similar radiopacity, with increased radiopacity, which comprises
    openings formed in at least the distal edges or ends of the device and
    a different marker material with greater radiopacity than the rest of the device of the device selected from the group comprising gold, gold alloys, tantalum, tantalum alloys, platinum, platinum alloys and other materials of similar radiopacity, compressed into said openings to form a rivet in each opening,
    wherein atoms from the device have migrated into the marker material and atoms from the marker material have migrated into the device.

6. The device of claim 5, wherein the atoms have migrated from 10 to 1000 Å.

7. The device of claim 5, which is a stent.

8. The device of claim 5, wherein there are at least two openings with a rivet in each opening.

9. The device of claim 5, wherein each opening is round and the rivet in each opening does not protrude from the outer surface of the stent.

10. The device of claim 5, wherein the respective edges of the opening are beveled.

11. The device of claim 5 further comprising a composite cover layer on the surface of the rivet, the composite cover layer comprising atoms from the device and atoms from the marker material.

12. In an implantable medical device, the improvement wherein the ends or edges of the device have openings and the openings contain markers comprised of material more radiopaque than the material of the device, wherein the devices have been heat treated so that atoms from the device migrate into the marker material and atoms from the marker material migrate into the device material.

13. A product prepared according to a process comprising the steps of:
    a) forming an implantable medical device produced from a material selected from the group comprising stainless steel 316L, nitinol, a cobalt-chromium alloy, and other materials of similar radiopacity;
    b) forming openings in at least the distal edges or ends of the device;
    c) inserting a different marker material with greater radiopacity then the rest of the device selected from the group comprising gold, gold alloys, tantalum, tantalum alloys, platinum, platinum alloys and other materials of similar radiopacity, into said openings to form a rivet in each opening; and
    d) heating the device from step c) for a sufficient time to cause atoms from the device to migrate into the marker material and atoms from the marker material to migrate into the device.

14. A method for increasing the radiopacity of an implantable medical device produced from a material selected from the group comprising stainless steel 316L, nitinol, a cobalt-chromium alloy, and other materials of similar radiopacity, which comprises the steps of
    (a) forming openings in at least the distal edges or ends of the device,
    (b) inserting a different marker material with greater radiopacity than the rest of the device selected from the group comprising gold, gold alloys, tantalum, tantalum alloys, platinum, platinum alloys and other materials of similar radiopacity, into said openings to form a rivet in each opening, and (c) heating the device under vacuum from about 700° C. to 1200° C. and for from about 1 minute to 2 hours.

15. The method of claim 14, wherein the heating is at from about $10^{-4}$ to $10^{-6}$ torr.

16. The method of claim 14, wherein the heating is from about 1050° C. to 1100° C.

17. The method of claim 14 wherein the heating is for from about 2 minutes to about 30 minutes.

* * * * *

UNITED STATES PATENT AND TRADEMARK OFFICE
CERTIFICATE OF CORRECTION

PATENT NO.    : 6,334,871 B1
DATED         : January 1, 2002
INVENTOR(S)   : Dor et al.

Page 1 of 1

It is certified that error appears in the above-identified patent and that said Letters Patent is hereby corrected as shown below:

<u>Title page,</u>
Item [56], References Cited, U.S. PATENT DOCUMENTS, after "5,080 674 A 01/1992", please delete "Jacobs" and insert -- Jacobs et al. --.

Signed and Sealed this

Nineteenth Day of November, 2002

Attest:

Attesting Officer

JAMES E. ROGAN
Director of the United States Patent and Trademark Office

UNITED STATES PATENT AND TRADEMARK OFFICE
CERTIFICATE OF CORRECTION

PATENT NO.    : 6,334,871 B1
DATED         : January 1, 2002
INVENTOR(S)   : Dor et al.

It is certified that error appears in the above-identified patent and that said Letters Patent is hereby corrected as shown below:

<u>Title page,</u>
Item [56], References Cited, U.S. PATENT DOCUMENTS, please insert
-- 4,733,665 B1 01/1994 Palmaz --

Signed and Sealed this

Twenty-fourth Day of December, 2002

JAMES E. ROGAN
*Director of the United States Patent and Trademark Office*